(12) United States Patent  
Rosser et al.

(10) Patent No.: US 11,838,997 B2  
(45) Date of Patent: Dec. 5, 2023

(54) CARTRIDGES FOR VAPORIZER DEVICES

(71) Applicant: JUUL Labs, Inc., San Francisco, CA (US)

(72) Inventors: Christopher James Rosser, Cambridge (GB); Samuel L. Stean, Cambridgeshire (GB)

(73) Assignee: JUUL Labs, Inc., Washington, DC (US)

( * ) Notice: Subject to any disclaimer, the term of this patent is extended or adjusted under 35 U.S.C. 154(b) by 812 days.

(21) Appl. No.: 16/674,721

(22) Filed: Nov. 5, 2019

(65) Prior Publication Data  
US 2020/0138117 A1 May 7, 2020

Related U.S. Application Data

(60) Provisional application No. 62/755,962, filed on Nov. 5, 2018.

(51) Int. Cl.  
A24F 40/10 (2020.01)  
A24F 40/42 (2020.01)  
A24F 40/485 (2020.01)  
H05B 3/44 (2006.01)  
F16J 15/44 (2006.01)  
A61M 11/04 (2006.01)  
A61M 15/00 (2006.01)

(52) U.S. Cl.  
CPC ............... H05B 3/44 (2013.01); A24F 40/10 (2020.01); A24F 40/42 (2020.01); A24F 40/485 (2020.01); A61M 11/042 (2014.02); A61M 15/0023 (2014.02); F16J 15/44 (2013.01); A61M 2205/276 (2013.01)

(58) Field of Classification Search  
CPC .............................. A24F 40/42; A24F 40/485  
USPC ........................................................ 131/329  
See application file for complete search history.

(56) References Cited

U.S. PATENT DOCUMENTS

| 4,036,224 A | 7/1977 | Choporis et al. |
| 4,163,038 A | 7/1979 | Kashihara et al. |
| 4,347,855 A | 9/1982 | Lanzillotti et al. |
| 4,399,349 A | 8/1983 | Deming et al. |

(Continued)

FOREIGN PATENT DOCUMENTS

| CA | 2518174 C | 11/2011 |
| CA | 2752134 C | 5/2015 |

(Continued)

Primary Examiner — Russell E Sparks  
(74) Attorney, Agent, or Firm — Mintz Levin Cohn Ferris Glovsy and Popeo, P.C.

(57) ABSTRACT

Cartridges for vaporizer devices are provided. In one exemplary embodiment, the cartridge can include a reservoir housing having a first housing end and a second housing end opposite the first housing end, an airflow tube that extends through the reservoir housing, and first and second seals that are each substantially impermeable to fluid, in which the first seal is substantially secured to the first housing end and the second seal is substantially secured to the second housing end. The reservoir housing is configured to hold vaporizable material and the first and second seals are configured to be selectively compromised to allow access to the vaporizable material within the reservoir housing for vaporization into vaporized material. Vaporizer devices are also provided.

20 Claims, 5 Drawing Sheets

(56) References Cited

U.S. PATENT DOCUMENTS

| | | |
|---|---|---|
| 4,619,297 A | 10/1986 | Kocher |
| 4,651,770 A | 3/1987 | Denham et al. |
| 4,735,217 A | 4/1988 | Gerth et al. |
| 4,818,843 A | 4/1989 | Swiatosz |
| 4,993,436 A | 2/1991 | Bloom, Jr. |
| 5,019,122 A | 5/1991 | Clearman et al. |
| 5,497,791 A | 3/1996 | Bowen et al. |
| 6,062,213 A | 5/2000 | Fuisz et al. |
| 6,098,632 A | 8/2000 | Turner et al. |
| 6,708,846 B1 | 3/2004 | Fuchs et al. |
| 6,769,436 B2 | 8/2004 | Horian |
| 6,909,840 B2 | 6/2005 | Harwig et al. |
| 7,243,689 B2 | 7/2007 | Py |
| 7,290,549 B2 | 11/2007 | Banerjee et al. |
| 7,793,860 B2 | 9/2010 | Bankers et al. |
| 7,793,861 B2 | 9/2010 | Bankers et al. |
| 7,913,686 B2 | 3/2011 | Hughes et al. |
| 8,003,080 B2 | 8/2011 | Rabinowitz et al. |
| 8,251,060 B2 | 8/2012 | White et al. |
| 8,314,591 B2 | 11/2012 | Terry et al. |
| 8,511,318 B2 | 8/2013 | Hon |
| 8,689,789 B2 | 4/2014 | Andrus et al. |
| 8,752,545 B2 | 6/2014 | Buchberger |
| 8,813,747 B2 | 8/2014 | Gibson et al. |
| 8,813,759 B1 | 8/2014 | Horian |
| 8,833,364 B2 | 9/2014 | Buchberger |
| 8,915,254 B2 | 12/2014 | Monsees et al. |
| 8,925,555 B2 | 1/2015 | Monsees et al. |
| 8,955,522 B1 | 2/2015 | Bowen et al. |
| 8,991,402 B2 | 3/2015 | Bowen et al. |
| 9,055,770 B2 | 6/2015 | Liu |
| 9,072,322 B2 | 7/2015 | Liu |
| 9,095,175 B2 | 8/2015 | Terry et al. |
| 9,132,248 B2 * | 9/2015 | Qiu .................... A24F 40/53 |
| 9,220,302 B2 | 12/2015 | DePiano et al. |
| 9,247,773 B2 | 2/2016 | Memari et al. |
| 9,277,770 B2 | 3/2016 | Depiano et al. |
| 9,308,336 B2 | 4/2016 | Newton |
| 9,427,022 B2 | 8/2016 | Levin et al. |
| 9,440,035 B2 | 9/2016 | Chung |
| 9,498,002 B1 | 11/2016 | Soreide et al. |
| 9,504,279 B2 | 11/2016 | Chen |
| 9,510,623 B2 | 12/2016 | Tucker et al. |
| 9,526,272 B2 | 12/2016 | Liu |
| 9,549,573 B2 | 1/2017 | Monsees et al. |
| 9,555,203 B2 | 1/2017 | Terry et al. |
| 9,609,893 B2 | 4/2017 | Novak et al. |
| 9,642,397 B2 | 5/2017 | Dai et al. |
| 9,648,908 B1 | 5/2017 | Rinehart et al. |
| 9,668,522 B2 | 6/2017 | Memari et al. |
| 9,675,109 B2 | 6/2017 | Monsees et al. |
| 9,675,118 B2 | 6/2017 | Chen |
| 9,681,688 B1 | 6/2017 | Rinehart et al. |
| 9,743,691 B2 | 8/2017 | Minskoff et al. |
| 9,770,055 B2 | 9/2017 | Cameron et al. |
| 9,814,265 B2 | 11/2017 | Rinker et al. |
| 9,820,508 B2 | 11/2017 | Schmiesing et al. |
| 9,833,021 B2 | 12/2017 | Perez et al. |
| 9,839,238 B2 | 12/2017 | Worm et al. |
| 9,861,135 B2 | 1/2018 | Chen |
| 9,888,721 B2 | 2/2018 | Chan |
| 9,936,733 B2 | 4/2018 | Ampolini et al. |
| 9,999,250 B2 | 6/2018 | Minskoff et al. |
| 10,034,988 B2 | 7/2018 | Wensley et al. |
| 10,045,567 B2 | 8/2018 | Monsees et al. |
| 10,045,568 B2 | 8/2018 | Monsees et al. |
| 10,058,124 B2 | 8/2018 | Monsees et al. |
| 10,058,130 B2 | 8/2018 | Monsees et al. |
| 10,070,669 B2 | 9/2018 | Monsees et al. |
| 10,076,139 B2 | 9/2018 | Monsees et al. |
| 10,080,387 B2 | 9/2018 | Phillips et al. |
| 10,085,485 B2 | 10/2018 | Hunt et al. |
| 10,092,713 B2 | 10/2018 | Terry et al. |
| 10,104,914 B2 | 10/2018 | Force |
| 10,104,915 B2 | 10/2018 | Bowen et al. |
| 10,111,461 B2 | 10/2018 | Balder et al. |
| 10,111,467 B1 | 10/2018 | Arnel et al. |
| 10,111,470 B2 | 10/2018 | Monsees et al. |
| 10,117,465 B2 | 11/2018 | Monsees et al. |
| 10,117,466 B2 | 11/2018 | Monsees et al. |
| 10,130,123 B2 | 11/2018 | Hatton et al. |
| 10,131,532 B2 | 11/2018 | Murison et al. |
| 10,159,278 B2 | 12/2018 | Minskoff et al. |
| 10,159,282 B2 | 12/2018 | Monsees et al. |
| 10,188,148 B2 | 1/2019 | Althorpe et al. |
| 10,201,190 B2 | 2/2019 | Monsees et al. |
| 10,206,429 B2 | 2/2019 | Davis et al. |
| 10,231,486 B2 | 3/2019 | Bowen et al. |
| 10,264,823 B2 | 4/2019 | Monsees et al. |
| 10,279,934 B2 | 5/2019 | Christensen et al. |
| 10,285,444 B2 | 5/2019 | Clemens et al. |
| 10,292,435 B2 | 5/2019 | Qiu |
| 10,299,513 B2 | 5/2019 | Perez et al. |
| 10,314,332 B2 | 6/2019 | Balder et al. |
| 10,383,368 B2 | 8/2019 | Larson |
| 10,412,996 B2 | 9/2019 | Bright et al. |
| 10,631,576 B1 | 4/2020 | Chen et al. |
| 10,874,139 B2 * | 12/2020 | Alvarez ................ A61M 15/06 |
| 10,940,274 B2 * | 3/2021 | Malhotra ............ A61M 15/004 |
| 11,006,667 B2 * | 5/2021 | Fornarelli ................ A24F 40/60 |
| 2001/0032643 A1 | 10/2001 | Hochrainer et al. |
| 2002/0059939 A1 | 5/2002 | Fox |
| 2002/0158351 A1 | 10/2002 | Wohrle |
| 2005/0066961 A1 | 3/2005 | Rand |
| 2005/0279353 A1 | 12/2005 | Mccoy |
| 2006/0026637 A1 | 2/2006 | Gatto et al. |
| 2006/0196518 A1 | 9/2006 | Hon |
| 2007/0102013 A1 | 5/2007 | Adams et al. |
| 2007/0119450 A1 | 5/2007 | Wharton et al. |
| 2008/0023003 A1 | 1/2008 | Rosenthal |
| 2009/0192443 A1 | 7/2009 | Collins, Jr. |
| 2009/0283103 A1 | 11/2009 | Nielsen et al. |
| 2010/0006113 A1 | 1/2010 | Urtsev et al. |
| 2010/0166396 A1 | 7/2010 | Xu et al. |
| 2010/0260491 A1 | 10/2010 | Pitz et al. |
| 2011/0040235 A1 | 2/2011 | Castel |
| 2011/0146174 A1 | 6/2011 | Selvaag |
| 2011/0277761 A1 | 11/2011 | Terry et al. |
| 2011/0277780 A1 | 11/2011 | Terry et al. |
| 2012/0247494 A1 | 10/2012 | Oglesby et al. |
| 2012/0248005 A1 | 10/2012 | Bergey |
| 2012/0255546 A1 | 10/2012 | Goetz et al. |
| 2012/0269497 A1 | 10/2012 | Hatten |
| 2012/0298676 A1 | 11/2012 | Cooks |
| 2012/0318882 A1 | 12/2012 | Abehasera |
| 2013/0056013 A1 | 3/2013 | Terry et al. |
| 2013/0078025 A1 | 3/2013 | Turgeman et al. |
| 2013/0115821 A1 | 5/2013 | Golko et al. |
| 2013/0146489 A1 | 6/2013 | Scatterday |
| 2013/0174842 A1 | 7/2013 | Young et al. |
| 2013/0180533 A1 | 7/2013 | Kim et al. |
| 2013/0327327 A1 | 12/2013 | Edwards et al. |
| 2014/0053952 A1 | 2/2014 | Genosar |
| 2014/0109921 A1 | 4/2014 | Chen |
| 2014/0150785 A1 | 6/2014 | Malik et al. |
| 2014/0158129 A1 | 6/2014 | Pratt et al. |
| 2014/0161301 A1 | 6/2014 | Merenda |
| 2014/0190496 A1 | 7/2014 | Wensley et al. |
| 2014/0253144 A1 | 9/2014 | Novak et al. |
| 2014/0261487 A1 | 9/2014 | Chapman et al. |
| 2014/0270729 A1 | 9/2014 | DePiano et al. |
| 2015/0007836 A1 | 1/2015 | Xu et al. |
| 2015/0020825 A1 | 1/2015 | Galloway et al. |
| 2015/0034104 A1 | 2/2015 | Zhou |
| 2015/0040929 A1 | 2/2015 | Hon |
| 2015/0059787 A1 | 3/2015 | Qiu |
| 2015/0102777 A1 | 4/2015 | Cooper |
| 2015/0114409 A1 | 4/2015 | Brammer et al. |
| 2015/0136158 A1 | 5/2015 | Stevens et al. |
| 2015/0144145 A1 | 5/2015 | Chang et al. |
| 2015/0150308 A1 | 6/2015 | Monsees et al. |
| 2015/0164146 A1 | 6/2015 | Li et al. |
| 2015/0201674 A1 | 7/2015 | Dooly et al. |
| 2015/0208731 A1 | 7/2015 | Malamud et al. |

(56) References Cited

U.S. PATENT DOCUMENTS

| | | |
|---|---|---|
| 2015/0216233 A1 | 8/2015 | Sears et al. |
| 2015/0216236 A1 | 8/2015 | Bless et al. |
| 2015/0216237 A1 | 8/2015 | Wensley et al. |
| 2015/0224268 A1 | 8/2015 | Henry et al. |
| 2015/0245654 A1 | 9/2015 | Memari et al. |
| 2015/0245655 A1 | 9/2015 | Memari et al. |
| 2015/0245657 A1 | 9/2015 | Memari et al. |
| 2015/0245659 A1 | 9/2015 | DePiano et al. |
| 2015/0245662 A1 | 9/2015 | Memari et al. |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2015/0257445 A1 | 9/2015 | Henry et al. |
| 2015/0257447 A1 | 9/2015 | Sullivan |
| 2015/0257451 A1 | 9/2015 | Brannon et al. |
| 2015/0258289 A1 | 9/2015 | Henry et al. |
| 2015/0282527 A1 | 10/2015 | Henry et al. |
| 2015/0282529 A1 | 10/2015 | Li et al. |
| 2015/0282530 A1 | 10/2015 | Johnson et al. |
| 2015/0289567 A1 | 10/2015 | Liu |
| 2015/0305403 A1 | 10/2015 | Coelho |
| 2015/0313282 A1 | 11/2015 | Ademe et al. |
| 2015/0320116 A1 | 11/2015 | Bleloch et al. |
| 2015/0328415 A1 | 11/2015 | Minskoff et al. |
| 2015/0336689 A1 | 11/2015 | Brown et al. |
| 2015/0342256 A1 | 12/2015 | Chen |
| 2015/0342258 A1 | 12/2015 | Chen |
| 2015/0351456 A1 | 12/2015 | Johnson et al. |
| 2015/0366265 A1 | 12/2015 | Lansing |
| 2015/0366267 A1 | 12/2015 | Liu |
| 2015/0374039 A1 | 12/2015 | Zhu |
| 2016/0058073 A1 | 3/2016 | Chen |
| 2016/0073677 A1 | 3/2016 | Uecker et al. |
| 2016/0109115 A1 | 4/2016 | Lipowicz |
| 2016/0120218 A1 | 5/2016 | Schennum et al. |
| 2016/0120226 A1 | 5/2016 | Rado et al. |
| 2016/0120227 A1 | 5/2016 | Levitz et al. |
| 2016/0128387 A1 | 5/2016 | Chen |
| 2016/0135504 A1 | 5/2016 | Li et al. |
| 2016/0135506 A1 | 5/2016 | Sanchez et al. |
| 2016/0143360 A1 | 5/2016 | Sanchez et al. |
| 2016/0143365 A1 | 5/2016 | Liu |
| 2016/0150824 A1 | 6/2016 | Memari et al. |
| 2016/0150828 A1 | 6/2016 | Goldstein et al. |
| 2016/0183597 A1 | 6/2016 | Li et al. |
| 2016/0192708 A1 | 7/2016 | DeMeritt et al. |
| 2016/0200463 A1 | 7/2016 | Hodges et al. |
| 2016/0212520 A1 | 7/2016 | Merenda |
| 2016/0213866 A1 | 7/2016 | Tan |
| 2016/0219934 A1 | 8/2016 | Li et al. |
| 2016/0219937 A1 | 8/2016 | Rado |
| 2016/0227837 A1 | 8/2016 | Hammel et al. |
| 2016/0227841 A1 | 8/2016 | Li et al. |
| 2016/0235124 A1 | 8/2016 | Krietzman |
| 2016/0249683 A1 | 9/2016 | Li et al. |
| 2016/0262459 A1 | 9/2016 | Monsees et al. |
| 2016/0278163 A1 | 9/2016 | Chen |
| 2016/0309785 A1 | 10/2016 | Holtz |
| 2016/0309789 A1 | 10/2016 | Thomas, Jr. |
| 2016/0325858 A1 | 11/2016 | Ampolini et al. |
| 2016/0331913 A1 | 11/2016 | Bourque |
| 2016/0332754 A1 | 11/2016 | Brown et al. |
| 2016/0345630 A1 | 12/2016 | Mironov et al. |
| 2016/0345631 A1 | 12/2016 | Monsees et al. |
| 2016/0353800 A1 | 12/2016 | Di Carlo |
| 2016/0360784 A1 | 12/2016 | Liu |
| 2016/0366935 A1 | 12/2016 | Liu |
| 2016/0366937 A1 | 12/2016 | Liu |
| 2016/0366945 A1 | 12/2016 | Rado |
| 2016/0366947 A1 | 12/2016 | Monsees et al. |
| 2017/0006915 A1 | 1/2017 | Li et al. |
| 2017/0006917 A1 | 1/2017 | Alvarez |
| 2017/0020192 A1 | 1/2017 | Fregonese et al. |
| 2017/0020194 A1 | 1/2017 | Rehders |
| 2017/0027223 A1 | 2/2017 | Eksouzian |
| 2017/0045994 A1 | 2/2017 | Murison et al. |
| 2017/0049152 A1 | 2/2017 | Liu |
| 2017/0049153 A1 | 2/2017 | Guo et al. |
| 2017/0065001 A1 | 3/2017 | Li et al. |
| 2017/0071249 A1 | 3/2017 | Ampolini et al. |
| 2017/0071258 A1 | 3/2017 | Li et al. |
| 2017/0071260 A1 | 3/2017 | Li et al. |
| 2017/0105451 A1 | 4/2017 | Fornarelli |
| 2017/0112190 A1 | 4/2017 | Buchberger |
| 2017/0119040 A1 | 5/2017 | Cameron |
| 2017/0119044 A1 | 5/2017 | Oligschlaeger et al. |
| 2017/0119058 A1 | 5/2017 | Cameron |
| 2017/0119060 A1 | 5/2017 | Li et al. |
| 2017/0135398 A1 | 5/2017 | Scott et al. |
| 2017/0150753 A1 | 6/2017 | Macko et al. |
| 2017/0156400 A1 | 6/2017 | Liu |
| 2017/0170439 A1 | 6/2017 | Jarvis et al. |
| 2017/0181467 A1 | 6/2017 | Cameron |
| 2017/0181468 A1 | 6/2017 | Bowen et al. |
| 2017/0196272 A1 | 7/2017 | Li et al. |
| 2017/0208863 A1 | 7/2017 | Phillips et al. |
| 2017/0208868 A1 | 7/2017 | Li et al. |
| 2017/0208869 A1 | 7/2017 | Xu et al. |
| 2017/0215479 A1 | 8/2017 | Kies |
| 2017/0231282 A1 | 8/2017 | Bowen et al. |
| 2017/0231286 A1 | 8/2017 | Borkovec et al. |
| 2017/0238617 A1 | 8/2017 | Scatterday |
| 2017/0251723 A1 | 9/2017 | Kobal et al. |
| 2017/0251729 A1 | 9/2017 | Li et al. |
| 2017/0261200 A1 | 9/2017 | Stultz |
| 2017/0280778 A1 | 10/2017 | Force |
| 2017/0283154 A1 | 10/2017 | Karles et al. |
| 2017/0297892 A1 | 10/2017 | Li et al. |
| 2017/0304563 A1 | 10/2017 | Adelson |
| 2017/0304567 A1 | 10/2017 | Adelson |
| 2017/0333650 A1 | 11/2017 | Buchberger et al. |
| 2017/0340003 A1* | 11/2017 | Batista ................. A24B 15/167 |
| 2017/0354186 A1 | 12/2017 | Johnson et al. |
| 2017/0367407 A1 | 12/2017 | Althorpe et al. |
| 2018/0022516 A1 | 1/2018 | Liu |
| 2018/0027878 A1 | 2/2018 | Dendy et al. |
| 2018/0027883 A1 | 2/2018 | Zuber et al. |
| 2018/0035718 A1 | 2/2018 | Liu |
| 2018/0064174 A1 | 3/2018 | Monsees et al. |
| 2018/0070641 A1 | 3/2018 | Batista et al. |
| 2018/0070648 A1 | 3/2018 | Monsees et al. |
| 2018/0077967 A1 | 3/2018 | Hatton et al. |
| 2018/0085551 A1 | 3/2018 | Krietzman |
| 2018/0092405 A1 | 4/2018 | Monsees et al. |
| 2018/0092406 A1 | 4/2018 | Monsees et al. |
| 2018/0117268 A1 | 5/2018 | Selby et al. |
| 2018/0154092 A1 | 6/2018 | Patoret |
| 2018/0184712 A1 | 7/2018 | Fraser et al. |
| 2018/0184722 A1 | 7/2018 | Murison et al. |
| 2018/0192700 A1 | 7/2018 | Fraser et al. |
| 2018/0199627 A1 | 7/2018 | Bowen et al. |
| 2018/0214645 A1 | 8/2018 | Reevell |
| 2018/0220707 A1 | 8/2018 | Biel et al. |
| 2018/0263288 A1 | 9/2018 | Goldstein et al. |
| 2018/0296777 A1 | 10/2018 | Terry et al. |
| 2018/0317557 A1 | 11/2018 | Monsees et al. |
| 2018/0360129 A1 | 12/2018 | Bowen et al. |
| 2018/0360130 A1 | 12/2018 | Bowen et al. |
| 2019/0000148 A1 | 1/2019 | Atkins et al. |
| 2019/0008212 A1 | 1/2019 | Atkins et al. |
| 2019/0037922 A1 | 2/2019 | Liu |
| 2019/0046745 A1 | 2/2019 | Nettenstrom et al. |
| 2019/0069599 A1 | 3/2019 | Monsees et al. |
| 2019/0099561 A1 | 4/2019 | Nettenstrom |
| 2019/0104767 A1 | 4/2019 | Hatton et al. |
| 2019/0200677 A1 | 7/2019 | Chong et al. |
| 2019/0223510 A1 | 7/2019 | Bowen et al. |
| 2019/0246693 A1 | 8/2019 | Nettenstrom et al. |
| 2019/0256231 A1 | 8/2019 | Atkins et al. |
| 2019/0289916 A1 | 9/2019 | Adam et al. |
| 2020/0022418 A1 | 1/2020 | Christopher et al. |

(56) References Cited

U.S. PATENT DOCUMENTS

| | | | |
|---|---|---|---|
| 2020/0128874 A1 | 4/2020 | Atkins et al. | |
| 2020/0221778 A1* | 7/2020 | Trzecieski | A24F 40/10 |
| 2021/0145050 A1* | 5/2021 | Ricketts | A61M 15/06 |

FOREIGN PATENT DOCUMENTS

| | | |
|---|---|---|
| CN | 101862038 A | 10/2010 |
| CN | 101557728 B | 4/2011 |
| CN | 102655773 A | 9/2012 |
| CN | 102754924 A | 10/2012 |
| CN | 103237469 A | 8/2013 |
| CN | 204070533 U | 1/2015 |
| CN | 104983076 A | 10/2015 |
| CN | 105764366 A | 7/2016 |
| CN | 106102492 A | 11/2016 |
| CN | 206390296 U | 8/2017 |
| CN | 206403201 U | 8/2017 |
| CN | 209090052 U | 7/2019 |
| EP | 1618803 A1 | 1/2006 |
| EP | 2952110 A1 | 12/2015 |
| EP | 3087853 A1 | 11/2016 |
| EP | 3103356 A1 | 12/2016 |
| EP | 3143882 A3 | 3/2017 |
| EP | 3143884 A3 | 4/2017 |
| EP | 3158881 A1 | 4/2017 |
| EP | 3205597 A1 | 8/2017 |
| EP | 2967154 B1 | 10/2018 |
| GB | 2550540 A | 11/2017 |
| JP | 2006524494 A | 11/2006 |
| KR | 100971178 B1 | 7/2010 |
| KR | 200461404 Y1 | 7/2012 |
| KR | 101893283 B1 | 8/2018 |
| KR | 102016848 B1 | 8/2019 |
| TW | 201438608 A | 10/2014 |
| UA | 88052 C2 | 9/2009 |
| WO | WO-9712639 A1 | 4/1997 |
| WO | WO-9904840 A1 | 2/1999 |
| WO | WO-2004064548 A1 | 8/2004 |
| WO | WO-2007117675 A2 | 10/2007 |
| WO | WO-2010140841 A2 | 12/2010 |
| WO | WO-2012026963 A2 | 3/2012 |
| WO | WO-2012059726 A2 | 5/2012 |
| WO | WO-2012164033 A1 | 12/2012 |
| WO | WO-2012174677 A1 | 12/2012 |
| WO | WO-2013020220 A1 | 2/2013 |
| WO | WO-2013040193 A2 | 3/2013 |
| WO | WO-2013110208 A1 | 8/2013 |
| WO | WO-2013113612 A1 | 8/2013 |
| WO | WO-2013165878 A1 | 11/2013 |
| WO | WO-2014040915 A1 | 3/2014 |
| WO | WO-2014067236 A1 | 5/2014 |
| WO | WO-2014110119 A1 | 7/2014 |
| WO | WO-2014150979 A2 | 9/2014 |
| WO | WO-2015032093 A1 | 3/2015 |
| WO | WO-2015037925 A1 | 3/2015 |
| WO | WO-2015070398 A1 | 5/2015 |
| WO | WO-2015070405 A1 | 5/2015 |
| WO | WO-2015120588 A1 | 8/2015 |
| WO | WO-2015157901 A1 | 10/2015 |
| WO | WO-2015165083 A1 | 11/2015 |
| WO | WO-2015184620 A1 | 12/2015 |
| WO | WO-2015196395 A1 | 12/2015 |
| WO | WO-2016000130 A1 | 1/2016 |
| WO | WO-2016000233 A1 | 1/2016 |
| WO | WO-2016023173 A1 | 2/2016 |
| WO | WO-2016026104 A1 | 2/2016 |
| WO | WO-2016026156 A1 | 2/2016 |
| WO | WO-2016029386 A1 | 3/2016 |
| WO | WO-2016033721 A1 | 3/2016 |
| WO | WO-2016049822 A1 | 4/2016 |
| WO | WO-2016049823 A1 | 4/2016 |
| WO | WO-2016049855 A1 | 4/2016 |
| WO | WO-2016050246 A1 | 4/2016 |
| WO | WO-2016054793 A1 | 4/2016 |
| WO | WO-2016079151 A1 | 5/2016 |
| WO | WO-2016058992 A3 | 6/2016 |
| WO | WO-2016082217 A1 | 6/2016 |
| WO | WO-2016090531 A1 | 6/2016 |
| WO | WO-2016106499 A1 | 7/2016 |
| WO | WO-2016108694 A1 | 7/2016 |
| WO | WO-2016112533 A1 | 7/2016 |
| WO | WO-2016118005 A1 | 7/2016 |
| WO | WO-2016119119 A1 | 8/2016 |
| WO | WO-2016123763 A1 | 8/2016 |
| WO | WO-2016127389 A1 | 8/2016 |
| WO | WO-2016127396 A1 | 8/2016 |
| WO | WO-2016127468 A1 | 8/2016 |
| WO | WO-2016128562 A1 | 8/2016 |
| WO | WO-2016138689 A1 | 9/2016 |
| WO | WO-2016141508 A1 | 9/2016 |
| WO | WO-2016141555 A1 | 9/2016 |
| WO | WO-2016150019 A1 | 9/2016 |
| WO | WO-2016154897 A1 | 10/2016 |
| WO | WO-2016154994 A1 | 10/2016 |
| WO | WO-2016165057 A1 | 10/2016 |
| WO | WO-2016179376 A1 | 11/2016 |
| WO | WO-2016184247 A1 | 11/2016 |
| WO | WO-2016193336 A1 | 12/2016 |
| WO | WO-2016178098 A3 | 2/2017 |
| WO | WO-2017033132 A1 | 3/2017 |
| WO | WO-2017035720 A1 | 3/2017 |
| WO | WO-2017042081 A1 | 3/2017 |
| WO | WO-2017045132 A1 | 3/2017 |
| WO | WO-2017071298 A1 | 5/2017 |
| WO | WO-2017072239 A1 | 5/2017 |
| WO | WO-2017072277 A1 | 5/2017 |
| WO | WO-2017082728 A1 | 5/2017 |
| WO | WO-2017093535 A1 | 6/2017 |
| WO | WO-2017097821 A1 | 6/2017 |
| WO | WO-2017108268 A1 | 6/2017 |
| WO | WO-2017113106 A1 | 7/2017 |
| WO | WO-2017114389 A1 | 7/2017 |
| WO | WO-2017122196 A1 | 7/2017 |
| WO | WO-2017144400 A1 | 8/2017 |
| WO | WO-2017163046 A1 | 9/2017 |
| WO | WO-2017167169 A1 | 10/2017 |
| WO | WO-2017167513 A1 | 10/2017 |
| WO | WO-2017173669 A1 | 10/2017 |
| WO | WO-2017205838 A1 | 11/2017 |
| WO | WO-2017207416 A1 | 12/2017 |
| WO | WO-2017207419 A1 | 12/2017 |
| WO | WO-2018048813 A1 | 3/2018 |
| WO | WO-2018165769 A1 | 9/2018 |
| WO | WO-2019173923 A1 | 9/2019 |
| WO | WO-2019232086 A1 | 12/2019 |
| WO | WO-2020025644 A1 | 2/2020 |

* cited by examiner

CARTRIDGES FOR VAPORIZER DEVICES

CROSS-REFERENCE TO RELATED APPLICATIONS

This application claims priority to U.S. Provisional Patent Application No. 62/755,962 filed on Nov. 5, 2018, and entitled "Cartridges For Vaporizer Devices," the disclosure of which is incorporated herein by reference in its entirety.

TECHNICAL FIELD

The subject matter described herein relates to vaporizer devices, including vaporizer cartridges.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizers are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer can be provided within a cartridge for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

An approach by which a vaporizer device generates an inhalable aerosol from a vaporizable material involves heating the vaporizable material in a vaporization chamber (e.g., a heater chamber) to cause the vaporizable material to be converted to the gas (or vapor) phase. A vaporization chamber can refer to an area or volume in the vaporizer device within which a heat source (for example, a conductive, convective, and/or radiative heat source) causes heating of a vaporizable material to produce a mixture of air and vaporized material to form a vapor for inhalation of the vaporizable material by a user of the vaporization device.

In some implementations, the vaporizable material can be drawn out of a reservoir and into the vaporization chamber via a wicking element (e.g., a wick). Drawing of the vaporizable material into the vaporization chamber can be at least partially due to capillary action provided by the wick as the wick pulls the vaporizable material along the wick in the direction of the vaporization chamber.

Vaporizer devices can be controlled by one or more controllers, electronic circuits (for example, sensors, heating elements), and/or the like on the vaporizer. Vaporizer devices can also wirelessly communicate with an external controller for example, a computing device such as a smartphone).

The vaporizable material used with a vaporizer device can be provided within a vaporizer cartridge. Once the vaporizer cartridge is manufactured and filled with the vaporizable material, it is then typically placed in secondary packaging, such as in a blister pack, for protection until subsequent use with the vaporizer device. The secondary packaging material used for the vaporizer cartridges generally inhibits chemical breakdown of the vaporizable material (e.g., by preventing exposure to ambient environment), and thus prolonging the shelf-life of the vaporizable material. Further, the secondary packaging material inhibits leakage of the vaporizable material that may occur prior to use.

However, the secondary packaging material itself can be expensive, and a significant amount may be needed to effectively package the cartridge. Further, once the vaporizer cartridge is removed from the secondary packaging material, the vaporizable material is exposed to ambient conditions outside of the cartridge and, if exposed for a substantial amount of time prior to use, the vaporizable material can begin to degrade. As a result, the shelf-life of the vaporizable material can be reduced drastically when removed from the secondary packaging too early. Additionally, once the vaporizer cartridge is removed, potential leakage of the vaporizable material can occur.

Accordingly, improved vaporizer devices and/or vaporizer cartridges that improve upon or overcome these issues is desired.

SUMMARY

Aspects of the current subject matter relate to vaporizer devices and to cartridges for use in a vaporizer device.

In some variations, one or more of the following features may optionally be included in any feasible combination.

In one exemplary embodiment, a cartridge for a vaporizer device is provided and includes a reservoir housing having a first housing end and a second housing end opposite the first housing end, an airflow tube that extends through the reservoir housing, and first and second seals that are each substantially impermeable to fluid. The reservoir housing is configured to hold vaporizable material. The airflow tube defines an airflow passageway therethrough. The first seal is substantially secured to the first housing end and the second seal is substantially secured to the second housing end, in which the first and second seals are configured to be selectively compromised to allow access to the vaporizable material within the reservoir housing for vaporization into vaporized material.

In some embodiments, the first seal can be configured to be pierced or removed from the first housing end.

In some embodiments, the second seal can be configured to be removed from the second housing end.

In some embodiments, the cartridge includes a cap. The cap can have a hollow cap body that can be configured to receive the second housing end. The cap can be secured to the second seal such that removal of the cap from the reservoir housing can remove the second seal from the second housing end of the reservoir housing.

In some embodiments, the fluid can be at least one of gas and liquid.

In some embodiments, the first and second seals can hermetically seal the reservoir housing.

The airflow tube can have a variety of configurations. For example, in some embodiments, the airflow tube can include a wicking element that is in communication with the reservoir chamber. The wicking element can be configured to substantially draw at least a portion of the vaporizable material from the reservoir chamber into the airflow passageway for vaporization.

In some embodiments, the cartridge can include a mouthpiece defining a hollow body and a hollow pin. The hollow body can include a first body end and a second body end opposing the first body end, in which first body end can include an orifice extending therethrough and the second body end can be configured to receive the first housing end. The hollow pin can extend distally from the first body end and in communication with the orifice. The mouthpiece and the reservoir housing can be configured to selectively slide relative to each other to cause a distal end of the hollow pin to pierce the first seal to thereby place the orifice in communication with the airflow passageway.

In some embodiments, the application of a compressive force to at least one of the mouthpiece and the reservoir housing can cause the hollow pin to move towards and the distal end thereof to pierce the first seal. In such embodiments, the cartridge can include a locking mechanism that can be configured to lock the mouthpiece to the reservoir housing so as to prevent the sliding of the mouthpiece and the reservoir housing relative to each other until the compressive force exceeds a predetermined threshold force.

In some embodiments, the cartridge can include a locking mechanism that can be configured to substantially secure the mouthpiece to the reservoir housing when a predetermined length of the hollow pin is received within the airflow tube.

The hollow pin can have a variety of configurations. For example, in some embodiments, the hollow pin can be axially aligned with the airflow tube such that piercing the first seal positions the hollow pin within at least a portion of the airflow tube.

In another exemplary embodiment, a vaporizer device is provided and includes a vaporizer body and a cartridge that is selectively coupled to and removable from the vaporizer body. The cartridge includes a reservoir housing having a first housing end and a second housing end opposite the first housing end, an airflow tube that extends through the reservoir housing, and first and second seals that are each substantially impermeable to fluid. The reservoir housing is configured to hold vaporizable material. The airflow tube defines an airflow passageway therethrough. The first seal is substantially secured to the first housing end and the second seal is substantially secured to the second housing end, in which the first and second seals are configured to be selectively compromised to allow access to the vaporizable material within the reservoir housing for vaporization into vaporized material.

In some embodiments, the vaporizer body can include a power source.

The cartridge can have a variety of configurations. For example, in some embodiments, the cartridge can include the cartridge can include a mouthpiece defining a hollow body and a hollow pin. The hollow body can include a first body end and a second body end opposing the first body end, in which first body end can include an orifice extending therethrough and the second body end can be configured to receive the first housing end. The hollow pin can extend distally from the first body end and in communication with the orifice. The mouthpiece and the reservoir housing can be configured to selectively slide relative to each other to cause a distal end of the hollow pin to pierce the first seal to thereby place the orifice in communication with the airflow passageway.

In some embodiments, the application of a compressive force to at least one of the mouthpiece and the reservoir housing can cause the hollow pin to move towards and the distal end thereof to pierce the first seal. In such embodiments, the cartridge can include a locking mechanism that can be configured to lock the mouthpiece to the reservoir housing so as to prevent the sliding of the mouthpiece and the reservoir housing relative to each other until the compressive force exceeds a predetermined threshold force.

In some embodiments, the cartridge can include a locking mechanism that can be configured to substantially secure the mouthpiece to the reservoir housing when a predetermined length of the hollow pin is received within the airflow tube.

The hollow pin can have a variety of configurations. For example, in some embodiments, the hollow pin can be axially aligned with the airflow tube such that piercing the first seal positions the hollow pin within at least a portion of the airflow tube.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated into and constitute a part of this specification, show certain aspects of the subject matter disclosed herein and, together with the description, help explain some of the principles associated with the disclosed implementations. In the drawings.

DETAILED DESCRIPTION

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizable material used with a vaporizer device can be provided within a cartridge (for example, a part of the vaporizer device that contains the vaporizable material in a reservoir or other container) which can be refillable when empty, or disposable such that a new cartridge containing additional vaporizable material of a same or different type can be used). A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material.

In some implementations, a vaporizer device can be configured for use with a liquid vaporizable material (for example, a carrier solution in which an active and/or inactive ingredient(s) are suspended or held in solution, or a liquid form of the vaporizable material itself). The liquid vaporizable material can be capable of being completely vaporized. Alternatively, at least a portion of the liquid vaporizable material can remain after all of the material suitable for inhalation has been vaporized.

Figure 1A:
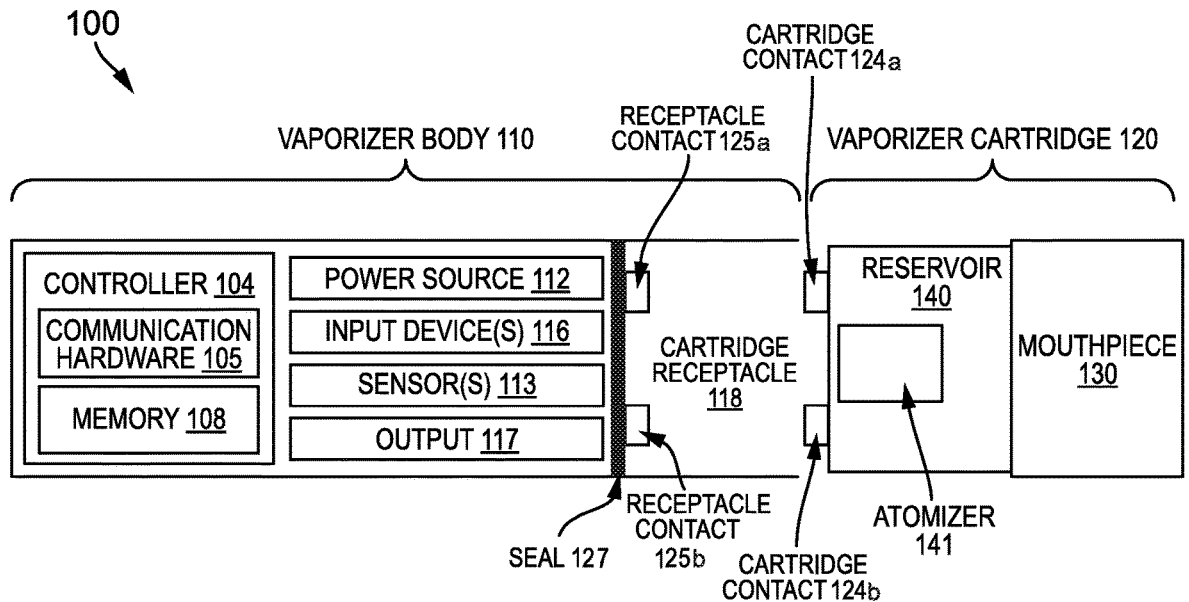
FIG. 1A is a block diagram of a vaporizer device.

Referring to the block diagram of FIG. 1A, a vaporizer device 100 can include a power source 112 (for example, a battery, which can be a rechargeable battery), and a controller 104 (for example, a processor, circuitry, etc. capable of executing logic) for controlling delivery of heat to an atomizer 141 to cause a vaporizable material 102 to be converted from a condensed form (such as a liquid, a solution, a suspension, a part of an at least partially unprocessed plant material, etc.) to the gas phase. The controller 104 can be part of one or more printed circuit boards (PCBs) consistent with certain implementations of the current subject matter.

After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer device and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The atomizer 141 in the vaporizer device 100 can be configured to vaporize a vaporizable material 102. The vaporizable material 102 can be a liquid. Examples of the vaporizable material 102 include neat liquids, suspensions, solutions, mixtures, and/or the like. The atomizer 141 can include a wicking element (i.e., a wick) configured to convey an amount of the vaporizable material 102 to a part of the atomizer 141 that includes a heating element (not shown in FIG. 1A).

For example, the wicking element can be configured to draw the vaporizable material 102 from a reservoir 140 configured to contain the vaporizable material 102, such that the vaporizable material 102 can be vaporized by heat delivered from a heating element. The wicking element can also optionally allow air to enter the reservoir 140 and replace the volume of vaporizable material 102 removed. In some implementations of the current subject matter, capillary action can pull vaporizable material 102 into the wick for vaporization by the heating element, and air can return to the reservoir 140 through the wick to at least partially equalize pressure in the reservoir 140. Other methods of allowing air back into the reservoir 140 to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer 141 can include a heating element which includes a resistive coil or other heating element wrapped around, positioned within, integrated into a bulk shape of, pressed into thermal contact with, or otherwise arranged to deliver heat to a wicking element, to cause the vaporizable material 102 drawn from the reservoir 140 by the wicking element to be vaporized for subsequent inhalation by a user in a gas and/or a condensed (for example, aerosol particles or droplets) phase. Other wicking elements, heating elements, and/or atomizer assembly configurations are also possible.

The heating element can be activated in association with a user puffing (i.e., drawing, inhaling, etc.) on a mouthpiece 130 of the vaporizer device 100 to cause air to flow from an air inlet, along an airflow path that passes the atomizer 141 (i.e., wicking element and heating element). Optionally, air can flow from an air inlet through one or more condensation areas or chambers, to an air outlet in the mouthpiece 130. Incoming air moving along the airflow path moves over or through the atomizer 141, where vaporizable material 102 in the gas phase is entrained into the air. The heating element can be activated via the controller 104, which can optionally be a part of a vaporizer body 110 as discussed herein, causing current to pass from the power source 112 through a circuit including the resistive heating element, which is optionally part of a vaporizer cartridge 120 as discussed herein. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece 130) for inhalation by a user.

Activation of the heating element can be caused by automatic detection of a puff based on one or more signals generated by one or more of a sensor 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (i.e., configurable on a screen or other display device and selectable via user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the resistive heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of a resistive heating element of the vaporizer device 100 can depend on a number of factors, including an amount of electrical power delivered to the resistive heating element and/or a duty cycle at which the electrical power is delivered, conductive heat transfer to other parts of the electronic vaporizer device 100 and/or to the environment, latent heat losses due to vaporization of the vaporizable material 102 from the wicking element and/or the atomizer 141 as a whole, and convective heat losses due to airflow (i.e., air moving across the heating element or the atomizer 141 as a whole when a user inhales on the vaporizer device 100). As noted herein, to reliably activate the heating element or heat the heating element to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element can be activated in association with a user's puff, for example by automatic detection of the puff, or by the sensor 113 detecting a change (such as a pressure change) in the airflow path.

The sensor 113 can be positioned on or coupled to (i.e., electrically or electronically connected, either physically or via a wireless connection) the controller 104 (for example, a printed circuit board assembly or other type of circuit board). To take measurements accurately and maintain durability of the vaporizer device 100, it can be beneficial to provide a seal 127 resilient enough to separate an airflow path from other parts of the vaporizer device 100. The seal 127, which can be a gasket, can be configured to at least partially surround the sensor 113 such that connections of the sensor 113 to the internal circuitry of the vaporizer device 100 are separated from a part of the sensor 113 exposed to the airflow path. In an example of a cartridge-based vaporizer device, the seal 127 can also separate parts of one or more electrical connections between the vaporizer body 110 and the vaporizer cartridge 120. Such arrangements of the seal 127 in the vaporizer device 100 can be helpful in mitigating against potentially disruptive impacts on vaporizer components resulting from interactions with environmental factors such as water in the vapor or liquid phases, other fluids such as the vaporizable material 102, etc., and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, excess vaporizable material 102, etc., in parts of the vaporizer device 100 where they can result in poor pressure signal, degradation of the sensor 113 or other components, and/or a shorter life of the vaporizer device 100. Leaks in the seal 127 can also result in a user inhaling air that has passed over parts of the vaporizer device 100 containing, or constructed of, materials that may not be desirable to be inhaled.

In some implementations, the vaporizer body 110 includes the controller 104, the power source 112 (for example, a battery), one more of the sensor 113, charging contacts (such as those for charging the power source 112), the seal 127, and a cartridge receptacle 118 configured to receive the vaporizer cartridge 120 for coupling with the vaporizer body 110 through one or more of a variety of attachment structures. In some examples, the vaporizer cartridge 120 includes the reservoir 140 for containing the vaporizable material 102, and the mouthpiece 130 has an aerosol outlet for delivering an inhalable dose to a user. The vaporizer cartridge 120 can include the atomizer 141 having a wicking element and a heating element. Alternatively, one or both of the wicking element and the heating element can be part of the vaporizer body 110. In implementations in which any part of the atomizer 141 (i.e., heating element and/or wicking element) is part of the vaporizer body 110, the vaporizer device 100 can be configured to supply vaporizable material 102 from the reservoir 140 in the vaporizer cartridge 120 to the part(s) of the atomizer 141 included in the vaporizer body 110.

In an embodiment of the vaporizer device 100 in which the power source 112 is part of the vaporizer body 110, and a heating element is disposed in the vaporizer cartridge 120 and configured to couple with the vaporizer body 110, the vaporizer device 100 can include electrical connection features (for example, means for completing a circuit) for completing a circuit that includes the controller 104 (for example, a printed circuit board, a microcontroller, or the like), the power source 112, and the heating element (for example, a heating element within the atomizer 141). These features can include one or more contacts (referred to herein as cartridge contacts 124a and 124b) on a bottom surface of the vaporizer cartridge 120 and at least two contacts (referred to herein as receptacle contacts 125a and 125b) disposed near a base of the cartridge receptacle 118 of the vaporizer device 100 such that the cartridge contacts 124a and 124b and the receptacle contacts 125a and 125b make electrical connections when the vaporizer cartridge 120 is inserted into and coupled with the cartridge receptacle 118. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts 124a and 124b and the receptacle contacts 125a and 125b can be configured to electrically connect in either of at least two orientations. In other words, one or more circuits necessary for operation of the vaporizer device 100 can be completed by insertion of the vaporizer cartridge 120 into the cartridge receptacle 118 in a first rotational orientation (around an axis along which the vaporizer cartridge 120 is inserted into the cartridge receptacle 118 of the vaporizer body 110) such that the cartridge contact 124a is electrically connected to the receptacle contact 125a and the cartridge contact 124b is electrically connected to the receptacle contact 125b. Furthermore, the one or more circuits necessary for operation of the vaporizer device 100 can be completed by insertion of the vaporizer cartridge 120 in the cartridge receptacle 118 in a second rotational orientation such cartridge contact 124a is electrically connected to the receptacle contact 125b and cartridge contact 124b is electrically connected to the receptacle contact 125a.

For example, the vaporizer cartridge 120 or at least the insertable end 122 of the vaporizer cartridge 120 can be symmetrical upon a rotation of 180° around an axis along which the vaporizer cartridge 120 is inserted into the cartridge receptacle 118. In such a configuration, the circuitry of the vaporizer device 100 can support identical operation regardless of which symmetrical orientation of the vaporizer cartridge 120 occurs.

In one example of an attachment structure for coupling the vaporizer cartridge 120 to the vaporizer body 110, the vaporizer body 110 includes one or more detents (for example, dimples, protrusions, etc.) protruding inwardly from an inner surface of the cartridge receptacle 118, additional material (such as metal, plastic, etc.) formed to include a portion protruding into the cartridge receptacle 118, and/or the like. One or more exterior surfaces of the vaporizer cartridge 120 can include corresponding recesses (not shown in FIG. 1A) that can fit and/or otherwise snap over such detents or protruding portions when the vaporizer cartridge 120 is inserted into the cartridge receptacle 118 on the vaporizer body 110. When the vaporizer cartridge 120 and the vaporizer body 110 are coupled (e.g., by insertion of the vaporizer cartridge 120 into the cartridge receptacle 118 of the vaporizer body 110), the detents or protrusions of the vaporizer body 110 can fit within and/or otherwise be held within the recesses of the vaporizer cartridge 120, to hold the vaporizer cartridge 120 in place when assembled. Such an assembly can provide enough support to hold the vaporizer cartridge 120 in place to ensure good contact between the cartridge contacts 124a and 124b and the receptacle contacts 125a and 125b, while allowing release of the vaporizer cartridge 120 from the vaporizer body 110 when a user pulls with reasonable force on the vaporizer cartridge 120 to disengage the vaporizer cartridge 120 from the cartridge receptacle 118.

In some implementations, the vaporizer cartridge 120, or at least an insertable end 122 of the vaporizer cartridge 120 configured for insertion in the cartridge receptacle 118, can have a non-circular cross section transverse to the axis along which the vaporizer cartridge 120 is inserted into the cartridge receptacle 118. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

The cartridge contacts 124a and 124b and the receptacle contacts 125a and 125b can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge 120 and the vaporizer body 110. The electrical contacts can optionally be gold-plated, and/or include other materials.

Figure 1B:
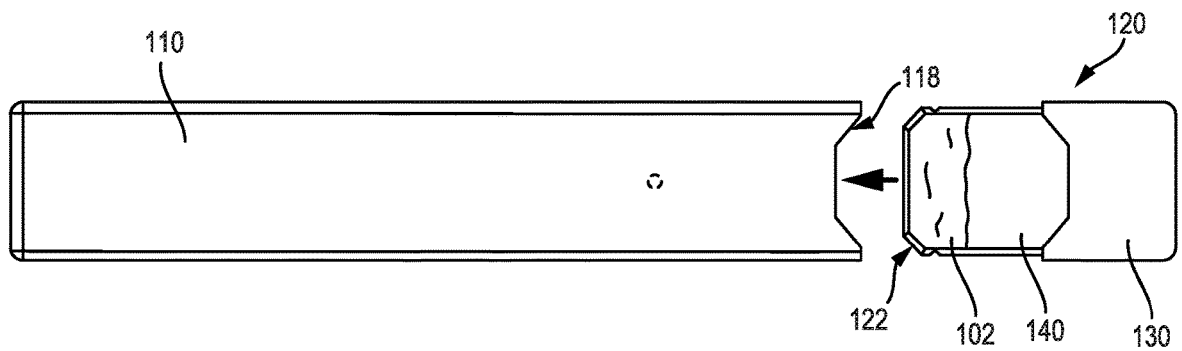
FIG. 1B is a top view of an embodiment of a vaporizer device, showing a vaporizer cartridge separated from a vaporizer device body.
Figure 1C:
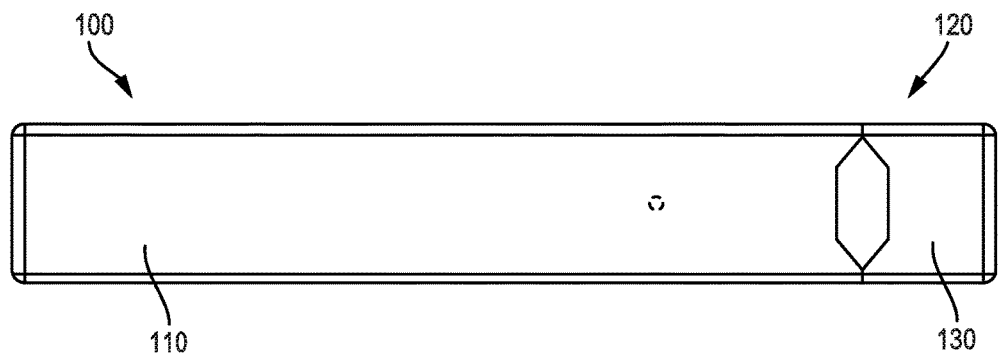
FIG. 1C is a top view of the vaporizer device of FIG. 1B, showing the vaporizer cartridge coupled to the vaporizer device body.
Figure 1D:
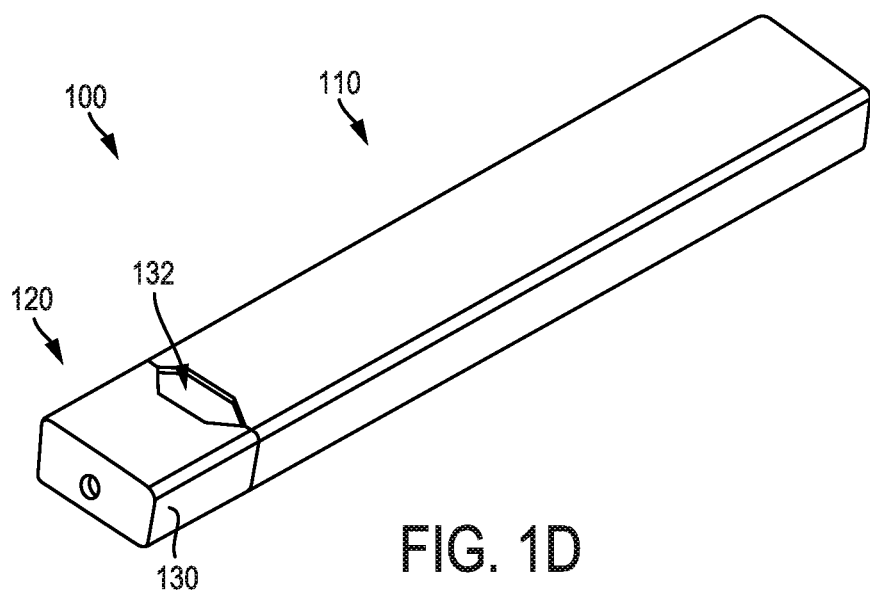
FIG. 1D is a perspective view of the vaporizer device of FIG. 1C.

FIGS. 1B-1D illustrate an embodiment of the vaporizer body 110 having a cartridge receptacle 118 into which the vaporizer cartridge 120 can be releasably inserted. FIGS. 1B and 1C show top views of the vaporizer device 100 illustrating the vaporizer cartridge 120 being positioned for insertion and inserted, respectively, into the vaporizer body 110. FIG. 1D illustrates the reservoir 140 of the vaporizer cartridge 120 being formed in whole or in part from translucent material such that a level of the vaporizable material 102 is visible from a window 132 (e.g., translucent material) along the vaporizer cartridge 120. The vaporizer cartridge 120 can be configured such that the window 132 remains visible when insertably received by the vaporizer cartridge receptacle 118 of the vaporizer body 110. For example, in one exemplary configuration, the window 132 can be disposed between a bottom edge of the mouthpiece 130 and a top edge of the vaporizer body 110 when the vaporizer cartridge 120 is coupled with the cartridge receptacle 118.

Figure 1E:
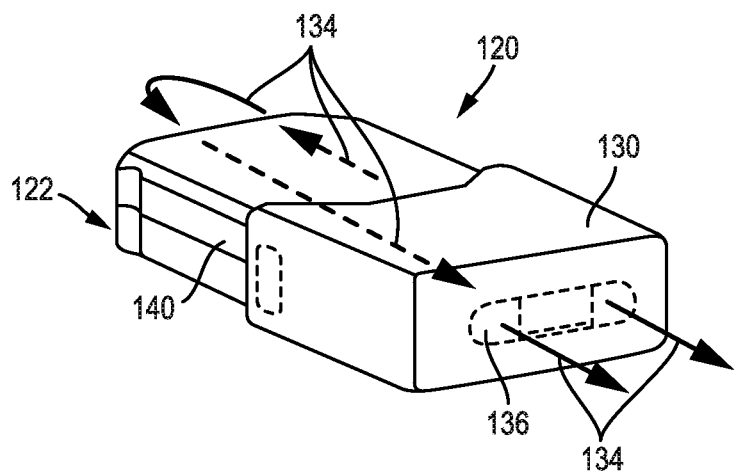
FIG. 1E is a perspective view of the vaporizer cartridge of FIG. 1B.

FIG. 1E illustrates an example airflow path 134 created during a puff by a user on the vaporizer device 100. The airflow path 134 can direct air to a vaporization chamber 150 (see FIG. 1F) contained in a wick housing where the air is combined with inhalable aerosol for delivery to a user via a mouthpiece 130, which can also be part of the vaporizer cartridge 120. For example, when a user puffs on the vaporizer device 100 device 100, air can pass between an outer surface of the vaporizer cartridge 120 (for example, window 132 shown in FIG. 1D) and an inner surface of the cartridge receptacle 118 on the vaporizer body 110. Air can then be drawn into the insertable end 122 of the vaporizer cartridge 120, through the vaporization chamber 150 that includes or contains the heating element and wick, and out through an outlet 136 of the mouthpiece 130 for delivery of the inhalable aerosol to a user.

As shown in FIG. 1E, this configuration causes air to flow down around the insertable end 122 of the vaporizer cartridge 120 into the cartridge receptacle 118 and then flow back in the opposite direction after passing around the insertable end 122 (e.g., an end opposite of the end including the mouthpiece 130) of the vaporizer cartridge 120 as it enters into the cartridge body toward the vaporization chamber 150. The airflow path 134 then travels through the interior of the vaporizer cartridge 120, for example via one or more tubes or internal channels (such as cannula 128 shown in FIG. 1F) and through one or more outlets (such as outlet 136) formed in the mouthpiece 130. The mouthpiece 130 can be a separable component of the vaporizer cartridge 120 or can be integrally formed with other component(s) of the vaporizer cartridge 120 (for example, formed as a unitary structure with the reservoir 140 and/or the like).

Figure 1F:
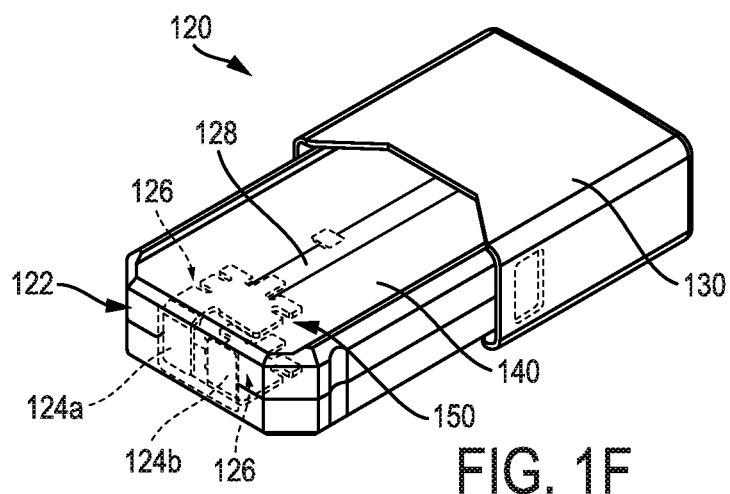
FIG. 1F is another perspective view of the vaporizer cartridge of FIG. 1E.

FIG. 1F shows additional features that can be included in the vaporizer cartridge 120 consistent with implementations of the current subject matter. For example, the vaporizer cartridge 120 can include a plurality of cartridge contacts (such as cartridge contacts 124a, 124b) disposed on the insertable end 122. The cartridge contacts 124a, 124b can optionally each be part of a single piece of metal that forms a conductive structure (such as conductive structure 126) connected to one of two ends of a resistive heating element. The conductive structure can optionally form opposing sides of a heating chamber and can act as heat shields and/or heat sinks to reduce transmission of heat to outer walls of the vaporizer cartridge 120. FIG. 1F also shows the cannula 128 within the vaporizer cartridge 120 that defines part of the airflow path 134 between the heating chamber formed between the conductive structure 126 and the mouthpiece 130.

As mentioned above, secondary packaging can be used to enclose existing vaporizer cartridges and protect the vaporizable material disposed therein from chemically breaking down, as well as leakage of the vaporizable material therefrom. The secondary packaging, however, can be expensive. Further, once the vaporizer cartridge is removed from the secondary packaging, the vaporizable material is exposed to the environment. As a result, the vaporizable material can begin to breakdown prior to cartridge use, thereby decreasing the shelf-life of the vaporizable material, and potentially negatively impact user experience. Further, once the vaporizer cartridge is removed from the secondary packaging, the vaporizable material can potentially leak from the cartridge and stain, or otherwise damage a user's clothing or possessions adjacent to a leaking cartridge (e.g., purse, etc.). Various features and devices are described below that improve upon or overcome these issues. For example, various features are described herein that provide integral cartridge sealing that inhibits exposure of the vaporizable material to the environment prior to use without the need for existing secondary packaging.

The vaporizer cartridges described herein employ barrier seals that prevent premature breaching of the seals prior to intended cartridge use. In some instances, the barrier seals are used in combination with an actuatable mechanism. The actuatable mechanisms described herein are capable of preserving the seals prior to the intended use of the vaporizer cartridge. This functionality preserves the shelf-life of the vaporizable material, as well as prevents potential leakage. The actuatable mechanisms are further capable, upon user activation, of breaching the barrier seals in a controlled manner which permits the vaporizable material contained therein to be vaporized on-demand. Further, the actuatable mechanisms can be user friendly yet child resistant, providing the level of safety comparable to secondary packaging.

The vaporizer cartridges generally include a reservoir housing, an airflow tube, and first and second seals. The first and second seals are secured to reservoir housing. In use, the first and second seals are compromised via joining of the vaporizer cartridge and the vaporizer body to allow access to the vaporizable material within the reservoir housing for vaporization into vaporized material.

The reservoir housing has a first housing end and a second housing end opposite the first housing end. The reservoir housing is configured to hold vaporizable material. The reservoir housing can be formed of a variety of materials having sufficient barrier properties to prevent at least egress of the vaporizable material therefrom. The reservoir housing material can also prevent ingress of water vapor and/or other gases (e.g., air) therein. Non-limiting examples of suitable reservoir housing material includes one or more polymers and copolymers. For example, the reservoir material can include one or more cyclic olefin copolymers, such as TOPAS, and the like.

The airflow tube extends through the reservoir housing and defines an airflow passageway therethrough. The airtube can have a variety of configurations (e.g., dimensions, geometry, such as cylindrical, rectangular, and the like, etc). Other airflow configurations are contemplated herein.

The airflow tube can include a wicking element that is in communication with the reservoir chamber. The wicking element is configured to substantially draw at least a portion of the vaporizable material from the reservoir chamber into the airflow passageway for vaporization. The wicking element can be further configured to be selectively bulked heated so as to vaporize at least a portion of the vaporizable material contained therein. The wicking element can be formed of any suitable material that can substantially draw the liquid vaporizable material into the airflow passageway of the airflow tube. As such, the wicking element is substantially porous. Non-limiting examples of suitable materials for the wicking element can include of one or more ceramic materials, one or more cottons, or one or more polymers. Such drawing of the vaporizable material into the airflow tube can be due, at least in part, to capillary action provided by the wicking element, which pulls the vaporizable material along the wick in the direction of the airflow tube.

The first and second seals are each substantially impermeable to fluid. The fluid can be gas and/or liquid. In one embodiment, the first and second seals hermetically seal the reservoir housing. The first and second seals can be formed of any material that inhibits fluid from passing therethrough. For example, the first and second seals are formed of material(s) that possess sufficient barrier properties that inhibit ingress of water vapor and/or other gasses into, as well as egress of the vaporizable material from, the reservoir housing. Non-limiting examples of suitable materials for the first and second seals include foil, polymers, and the like. The first and second seals can be formed of the same material(s) or different material(s). The first seal and/or the second seal can be single layered or multi-layered. Further, the first and second seal materials are compatible with the reservoir housing material (e.g., one or more cyclic olefin copolymers).

The first and second seals are substantially secured to the reservoir housing. The first seal can be substantially secured to the first housing end and the second seal can be substantially secured to the second housing end. The first and second seals can be substantially secured to the reservoir housing using a variety of the methods, such as heat sealing, adhesives, and the like.

The first and second seals can be substantially secured to the reservoir housing so as inhibit ingress of materials therein, as well as, inhibit vaporizable material disposed within the reservoir housing from leaking out. That is, the first and second seals are substantially secured to the reservoir housing so as to substantially isolate the vaporizable material from the ambient environment until intended use of the cartridge. In doing so, the first and second seals can also substantially seal the airflow path of the cartridge, which is at least partially defined through the reservoir housing.

As mentioned above, the first and second seals are configured to be compromised to allow access to the vaporizable material disposed within the reservoir housing. For example, a user can peel off the first seal and/or the second seals from the previous housing immediately before cartridge use. In some embodiments, the cartridge can include a cap having a hollow cap body that is configured to receive the second housing end. The cap can be secured to the second seal (e.g., by heating sealing or by an adhesive) such that removal of the cap from the reservoir housing removes the second seal from the second housing end of the reservoir housing.

Alternatively, or in addition, a user can actuate an actuatable mechanism of the cartridge to pierce the first seal. For example, the cartridge can include a mouthpiece having an orifice extending therethrough, and a hollow pin extending from the mouthpiece. The mouthpiece and the reservoir housing can be configured to selectively slide relative to each other to cause a distal end of the hollow pin to pierce the first seal to thereby place the orifice in communication with the airflow passageway of the airflow tube. Thus, in use, a user can apply a compressive force to at least one of the mouthpiece and the reservoir housing causes the hollow pin to move towards and the distal end thereof to pierce the first seal.

The mouthpiece can have a variety of configurations. In some embodiments, the mouthpiece defines a hollow body. The hollow body can include a first body end and a second body end opposing the first body end. The first body end can include the mouthpiece orifice, which extends therethrough, and the second body end can be configured to receive the first housing end of the reservoir housing. The orifice is configured to allow at least a portion of air and vaporized material to flow therethrough and out of the mouthpiece. The orifice can have a variety of configurations (e.g., dimensions, geometry, etc.). In some embodiments, the mouthpiece can include two or more orifices.

The hollow pin is in communication with the orifice. The hollow pin can have a variety of configurations (e.g., dimensions, geometry, etc.). The distal end of the hollow pin is configured to at least partially penetrate and pass through the first seal. For example, in some embodiments, the distal end can have a c-shaped configuration. In other embodiments, the distal end can be taper linearly. In one embodiment, the hollow pin can be axially aligned with the airflow tube such that piercing the first seal positions the hollow pin within at least a portion of the airflow tube. In this way, the pierced foil can be folded back and substantially pinned between the hollow pin and the airflow tube.

In some embodiments, the cartridge can include a locking mechanism (a first locking mechanism) that is configured to lock the mouthpiece to the reservoir housing so as to prevent the sliding of the mouthpiece and the reservoir housing relative to each other until the compressive force exceeds a predetermined threshold force. In this way, the locking mechanism can function as a safety feature (e.g., child resistant). The locking mechanism can have a variety of configurations. In one embodiment, the locking mechanism can include at least one tab that extends between the reservoir housing and the mouthpiece (e.g., between a sidewall of the housing and an inner surface of the hollow body). The at least one tab can possess sufficient rigidity to withstand a compressive force that is less than the predetermined threshold force. And, when the predetermined threshold force is met, the at least one tab can break or bend to allow the hollow pin to move towards and pierce the first seal. In another embodiment, the locking mechanism can include male and female elements positioned on the reservoir housing and the mouthpieces, respectively (or vice versa). These elements can be configured to be disengaged when a user applied a compressive force that is equal to or greater than the predetermined threshold force. Other suitable configurations for the locking mechanism is contemplated herein.

Alternatively, or in addition, the cartridge can include a locking mechanism (a second locking mechanism) that is configured to substantially secure the mouthpiece to the reservoir housing when a predetermined length of the hollow pin is received within the airflow tube. In this way, the second locking mechanism, when engaged, can substantially inhibit the hollow pin from retracting out of the reservoir housing once the first seal is pierced. The second locking mechanism can have a variety of configurations. In some embodiments, the second locking mechanism can include a first locking element of the reservoir housing and a second locking element of the mouthpiece. The first and second locking elements can be initially disengaged, and then become engaged once the predetermined length of the hollow pin is received within the airflow tube. For example, in one embodiment, the reservoir housing includes two protrusions extending therefrom (e.g., from opposing sidewalls of the reservoir housing) and the hollow body can include two corresponding recesses that are configured to engage the two protrusions as the mouthpiece (or reservoir housing) slides upon actuation by the user.

In some embodiments, the cartridge can include a heating element that is configured to vaporize at least a portion of the vaporizable material that is drawn from the reservoir housing into the airflow passageway via the wicking element. For example, in some embodiments, the heating element can be contained within the airflow tube and wrapped around, positioned within, integrated into a bulk shape of, pressed into thermal contact with, or otherwise arranged to deliver heat to the wicking element. In this way, when the first and second seals are compromised, at least a portion of the vaporizable material that is drawn from the reservoir housing into the airflow passageway by the wicking element can then be vaporized into the vaporized material. The vaporized material can then mix with, and be carried out of the airflow tube by, air passing through the airflow passageway.

Figure 2:
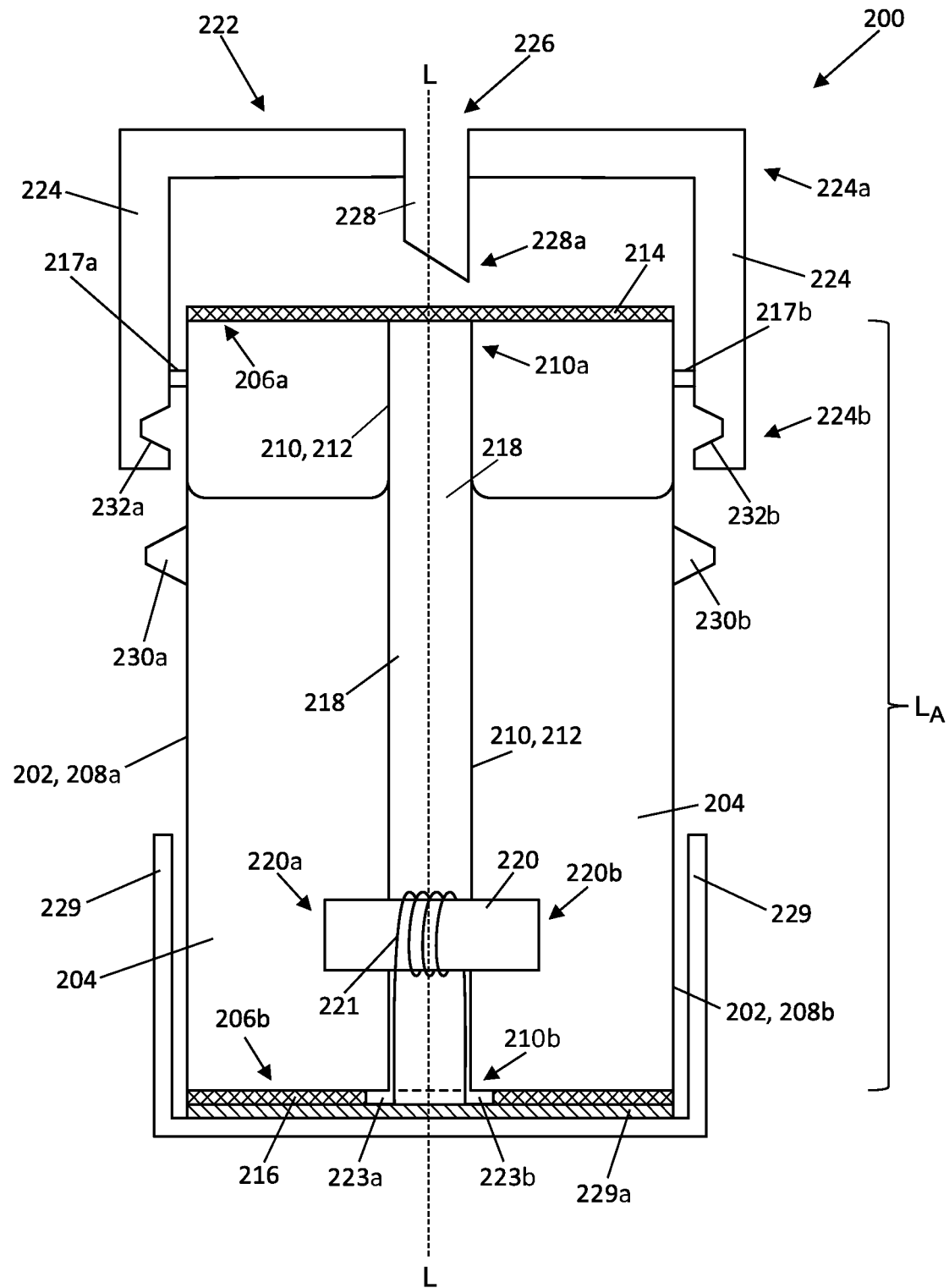
FIG. 2 is a schematic cross-sectional view of another embodiment of a vaporizer cartridge, showing the vaporizer cartridge in a pre-actuated state.
Figure 3:
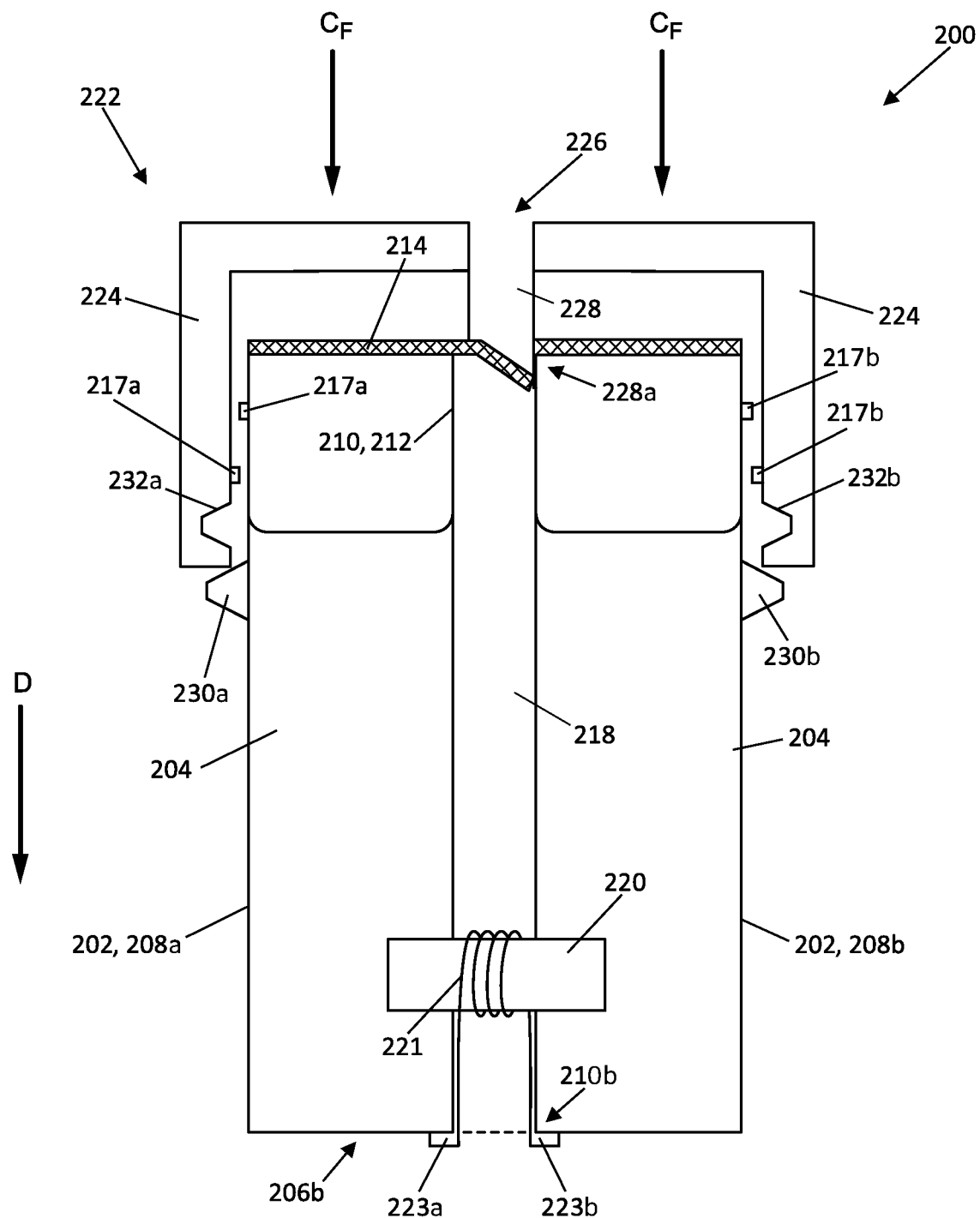
FIG. 3 is a schematic cross-sectional view of the cartridge of FIG. 2, showing the vaporizer cartridge in an intermediate actuated position.
Figure 4:
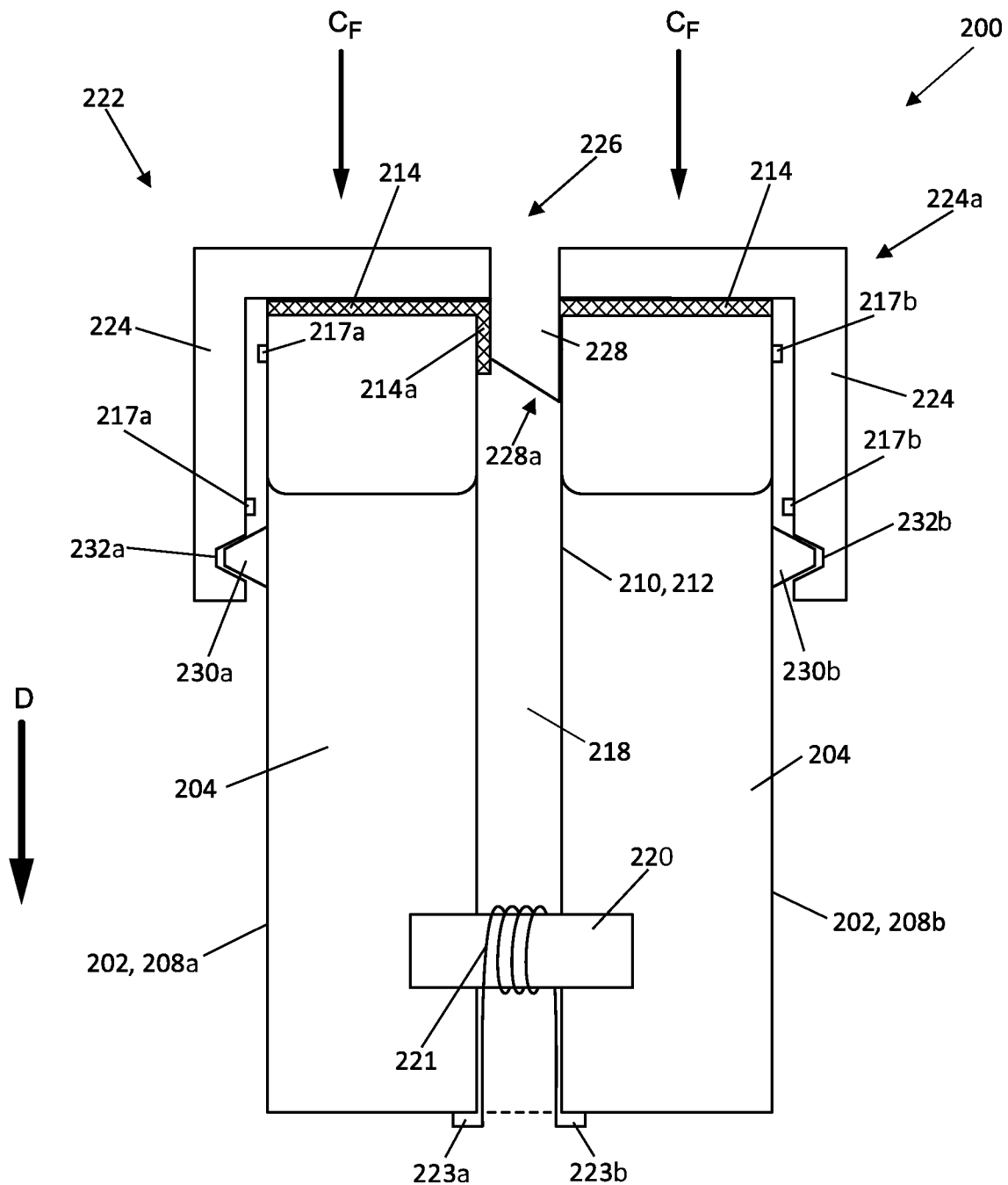
FIG. 4 is a schematic cross-sectional view of the cartridge of FIG. 2, showing the vaporizer cartridge in a completely actuated position.

FIGS. 2-4 illustrate an exemplary vaporizer cartridge 200 that can be selectively coupled to and removable from a vaporizer body, such as vaporizer body 110 shown in FIGS. 1A-1D. More specifically, the vaporizer cartridge 200 includes a reservoir housing 202, an airflow tube 210 extending through the reservoir housing 202, first and second seals 214, 216, a mouthpiece 222, and a hollow pin 228 extending therefrom. An exemplary actuation sequence using an exemplary actuation mechanism is shown in FIGS. 2-4, in which the vaporizer cartridge 200 is in a pre-actuated position in FIG. 2, in an intermediate actuated position in FIG. 3, and in a completely actuated position in FIG. 4. For purposes of simplicity, certain components of the vaporizer cartridge 200 are not illustrated.

As shown, the reservoir housing 202 contains a vaporizable material 204. The reservoir housing 202 is defined by two opposing ends (two opposing housing ends) 206a, 206b and two opposing sidewalls 208a, 208b. While the reservoir housing 202 can have a variety of shapes and sizes, the reservoir housing 202, as shown in FIGS. 2-4, is substantially rectangular in shape. Other shapes and sizes of the reservoir housing 202 are contemplated herein.

While the airflow tube 210 is shown to be approximately centered within respect to a longitudinal axis (L) extending through a centroid of the reservoir housing 202, such position is not required. As such, other locations of the airflow tube 210 within the reservoir housing 202 are also contemplated herein. Further, other airflow configurations through the reservoir housing 202 are also contemplated herein.

The airflow tube 210 can have a variety of configurations. For example, as shown in FIGS. 2-4, the airflow tube 210 extends a length (LA) from a first end 210a to a second end 210b and is defined by a curved sidewall 212. Further, the airflow tube 210 defines an airflow passageway 218 that extends therethrough. The airflow passageway 218, and thus the airflow tube 210, is configured to receive the vaporizable material 204. As described above, vaporizable material 204 entering the airflow passageway 218 is then vaporized to form a vaporized material.

As further shown in FIGS. 2-4, the airflow tube 210 includes a wicking element 220. As discussed above, the wicking element 220 is configured to draw a portion of the vaporizable material 204 from the reservoir housing 202 into the airflow tube 210 for vaporization. Further, as discussed above, the wicking element 220 can also be further configured to be selectively bulk heated, e.g., by a heating element (not shown), so as to vaporize the portion of vaporizable material 204.

While the wicking element 220 can have a variety of configurations, the wicking element 220 is substantially rectangular. The wicking element 220 extends substantially laterally across the airflow tube 210 (e.g., substantially perpendicular to the length (LA) of the airflow tube 210) such that a first and a second opposing end 220a, 220b of the wicking element 220 are each positioned within the reservoir housing 202. As such, the wicking element 220 is in fluid communication with the reservoir housing 202.

Further, as shown in FIGS. 2-4, the vaporizer cartridge 200 includes a heating element 221 is disposed within the airflow tube 210. The heating element 221 is configured to vaporize at least a portion of the vaporizable material that is drawn from the reservoir housing 202 into the wicking element 220. The heating element 221 can be or include one or more of a conductive heater, a radiative heater, and a convective heater. As discussed above, one type of heating element is a resistive heating element, such as a resistive coil, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. As shown in FIGS. 2-4, the heating element 221 is in the form of a resistive coil.

In some embodiments, the vaporizer cartridge 200 includes two or more cartridge contacts such as, for example, a first cartridge contact 223a and a second cartridge contact 223b. The two or more cartridge contacts can be configured to couple, for example, with the receptacle contacts 125a and 125b in order to form one or more electrical connections with the vaporizer body 110. The circuit completed by these electrical connections can allow delivery of electrical current to the heating element 221. The circuit can also serve additional functions such as, for example, measuring a resistance of the heating element 221 for use in determining and/or controlling a temperature of the heating element 221 based on a thermal coefficient of resistivity of the heating element 221.

As shown in FIG. 2, the first and second seals 214, 216 are substantially secured to the two opposing housing ends 206a, 206b. That is, the first seal 214 is substantially secured to the first housing end 206a and the second seal 216 is substantially secured to the second housing end 206b. The first and second seals 214, 216 extend across the first and second housing ends 206a, 206b so as to substantially seal the airflow passageway 218. As described above, the first and second seals 214, 216 are substantially impermeable to fluid. In this way, the vaporizable material 204 is isolated from the environment outside of the vaporizer cartridge 200 and is substantially inhibited from inadvertently expelling out of the vaporizer cartridge 200 when the first and second seals 214, 216 are substantially intact and substantially secured to the reservoir housing 202.

As shown in FIG. 2, the mouthpiece 222 is initially coupled to the vaporizer cartridge 200 via a first locking mechanism. While the first locking mechanism can have a variety of configurations, in this illustrated embodiment, the first locking mechanism includes a first tab 217a that extends between the mouthpiece 222 and the sidewall 208a of the reservoir housing 202 and a second tab 217b that extends between the mouthpiece 222 and the sidewall 208b of the reservoir housing 202. The first tab 217a and the second tab 217b are each configured to secure the mouthpiece 222 to the reservoir housing 202 until a compressive force is applied to the mouthpiece that exceeds a predetermined threshold force. That is, the first tab 217a and the second tab 217b each possess sufficient rigidity to withstand a compressive force that is less than the predetermined threshold force. And, when the predetermined threshold force is met, the compressive force causes the first tab 217a and the second tab 217b to break, as shown in FIG. 3. This allows the hollow pin to move further towards and pierce the first seal.

As further shown in the FIGS. 2-4, the mouthpiece 222 includes a hollow body 224. The hollow body 224 has a first body end 224a and a second body end 224b. The first body end 224a includes an orifice 226 extending therethrough. While the mouthpiece 222 and the reservoir housing 202 can be coupled together using a first locking mechanism as described above.

While the hollow pin 228 can have a variety of configurations, the hollow pin 228, as shown in FIGS. 2-4, the hollow pin 228 extends from the first body end 224a. As such, the hollow pin 228 is in communication with the orifice 226. In this illustrated embodiment, the hollow pin 228 has a substantially cylindrical shape and includes a linearly tapered distal end 228a. As discussed above, the distal end 228a is configured to pierce at least a portion of the first seal 214. In use, once the distal end 228a pierces through at least a portion of the first seal 214, the hollow pin 228, and thus the orifice 226 of the mouthpiece 222, is in fluid communication with the airflow passageway 218. In this illustrated embodiment, the hollow pin 228 is also shown as being axially aligned with the airflow tube 210.

Further, the vaporizer cartridge 200 includes a second locking mechanism. The second locking mechanism includes two protrusions 230a, 230b extending outwardly from the two opposing sidewalls 208a, 208b of the reservoir housing 202 and two corresponding recess channels 232a, 232b extending inward into the hollow body 224. The position of the second locking mechanism is dependent at least upon the predetermined length of the hollow pin 228 that is to be received within the airflow tube 210 and the structural configuration of the mouthpiece 222. Other configurations of suitable second locking mechanisms are also contemplated herein.

As shown in FIGS. 2-4, as a compressive force ($C_F$) is applied (e.g., by a user) to the mouthpiece 222, the mouthpiece 222 slides in a distal direction (D) along the reservoir housing 202 thereby urging the hollow pin 228 towards the first seal 214. This causes the hollow pin 228 to begin to pierce the first seal 214, as shown in FIG. 3. As a result, the hollow pin 228, and thus the orifice 226 of the mouthpiece 222 is then in fluid communication with the airflow passageway 218.

It will be appreciated that the second seal 216 can be removed from the second housing end 206b prior to, during, or subsequent to, the application of the compressive force ($C_F$). In this illustrated embodiment, the second seal 216 is removed prior to the application of the compressive force ($C_F$). As such, the second seal 216 is not illustrated in FIGS. 3-4. The second seal 216 can be removed in a variety of ways. In this illustrated embodiment, a cap 229 is selectively coupled to and removable from the vaporizer cartridge 200. In this example, the cap 229 is secured to the second seal 216 via an adhesive 229a. Thus, in use, the removal of the cap 229 from the reservoir housing 202 (e.g., by grasping the cap 229 and pulling the cap 229 in a direction away from the vaporizer cartridge 200) concurrently removes the second seal 216 from the second housing end 206b of the reservoir housing 202.

As the compressive force ($C_F$) continues to be applied to the mouthpiece 222 (e.g., by the user), the hollow pin 228 continues to pierce through the first seal 214 until a predetermined length of the hollow pin 228 within the airflow tube 210 has been reached (e.g., also when the first body end 224a of the hollow body 224 comes into contact with the remaining portion of the first seal 214), as shown in FIG. 4. Also, the user can receive tactile feedback in response to the engagement of the second locking mechanism and cease application of the compressive force ($C_F$). As shown in FIG. 4, after complete actuation, the pierced foil 214a is pinned between the hollow pin 228 and the airflow tube 210. Further, as shown in FIG. 4, maximum fluid communication between the orifice 226 and the airflow passageway 218 has been reached. While maximum communication is desired for effective use of the vaporizer cartridge 200, it is not necessary. That is, complete actuation of the actuation mechanism is not necessary, although desired, to expose the vaporizable material 204 to the environment, and ultimately allow the vaporizable material 204 to be vaporized.

Terminology

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. A cartridge for a device, the cartridge comprising:
    a reservoir housing having a first housing end and a second housing end opposite the first housing end, the reservoir housing being configured to hold vaporizable material;
    an airflow tube that extends through the reservoir housing, the airflow tube defining an airflow passageway therethrough;
    first and second seals that are each substantially impermeable to fluid, the first seal being substantially secured to the first housing end and the second seal being substantially secured to the second housing end, wherein the first and second seals are configured to be selectively compromised to allow access to the vaporizable material within the reservoir housing for vaporization into vaporized material;
    a mouthpiece defining a hollow body, the hollow body including a first body end and a second body end opposing the first body end, the first body end including an orifice extending therethrough and the second body end being configured to receive the first housing end;
    a hollow pin extending distally from the first body end and in communication with the orifice, wherein the mouthpiece and the reservoir housing are configured to selectively slide relative to each other to cause a distal end of the hollow pin to pierce the first seal to thereby place the orifice in communication with the airflow passageway; and
    a locking mechanism configured to lock the mouthpiece to the reservoir housing so as to prevent the sliding of the mouthpiece and the reservoir housing relative to each other until application of a compressive force to at least one of the mouthpiece and the reservoir housing exceeds a predetermined threshold force;
    wherein the mouthpiece is locked to the reservoir housing of the cartridge during insertion or removal of at least a portion of the cartridge into or from the device.

2. The cartridge of claim 1, wherein the first seal is configured to be removed from the first housing end.

3. The cartridge of claim 1, wherein the second seal is configured to be removed from the second housing end.

4. The cartridge of claim 1, further comprising a cap having a hollow cap body that is configured to receive the second housing end.

5. The cartridge of claim 4, wherein the cap is secured to the second seal such that removal of the cap from the reservoir housing removes the second seal from the second housing end of the reservoir housing.

6. The cartridge of claim 1, wherein the fluid is at least one of gas and liquid.

7. The cartridge of claim 1, wherein the first and second seals hermetically seal the reservoir housing.

8. The cartridge of claim 1, wherein the airflow tube includes a wicking element that is in communication with the reservoir housing, and wherein the wicking element is configured to substantially draw at least a portion of the vaporizable material from the reservoir housing into the airflow passageway for vaporization.

9. The cartridge of claim 1, wherein application of a compressive force to at least one of the mouthpiece and the reservoir housing causes the hollow pin to move towards and the distal end thereof to pierce the first seal.

10. The cartridge of claim 1, wherein the hollow pin is axially aligned with the airflow tube such that piercing the first seal positions the hollow pin within at least a portion of the airflow tube.

11. The cartridge of claim 1, furthering comprising another locking mechanism that is configured to substantially secure the mouthpiece to the reservoir housing when a predetermined length of the hollow pin is received within the airflow tube.

12. A device, comprising:
    a vaporizer body; and
    a cartridge that is selectively coupled to and removable from the vaporizer body, the cartridge including:
        a reservoir housing having a first housing end and a second housing end opposite the first housing end, the reservoir housing being configured to hold vaporizable material,
        an airflow tube that extends through the reservoir housing, the airflow tube defining an airflow passageway therethrough,
        first and second seals that are each substantially impermeable to fluid, the first seal being substantially secured to the first housing end and the second seal being substantially secured to the second housing end, wherein the first and second seals are configured to be selectively compromised to allow access to the vaporizable material within the reservoir housing for vaporization into vaporized material, a mouthpiece defining a hollow body, the hollow body including a first body end and a second body end opposing the first body end, the first body end including an orifice extending therethrough and the second body end being configured to receive the first housing end, a hollow pin extending distally from the first body end and in communication with the orifice; wherein the mouthpiece and the reservoir housing are configured to selectively slide relative to each other to cause a distal end of the hollow pin to pierce the first seal to thereby place the orifice in communication with the airflow passageway, and a locking mechanism configured to lock the mouthpiece to the reservoir housing so as to prevent the sliding of the mouthpiece and the reservoir housing relative to each other until application of a compressive force to at least one of the mouthpiece and the reservoir housing exceeds a predetermined threshold force;

wherein the mouthpiece is locked to the reservoir housing of the cartridge during insertion or removal of at least a portion of the cartridge into or from the device.

13. The device of claim 12, wherein the vaporizer body includes a power source.

14. The device of claim 12, wherein application of a compressive force to at least one of the mouthpiece and the reservoir housing causes the hollow pin to move towards and the distal end thereof to pierce the first seal.

15. The device of claim 12, wherein the hollow pin is axially aligned with the airflow tube such that piercing the first seal positions the hollow pin within at least a portion of the airflow tube.

16. The device of claim 12, wherein the cartridge further comprises another locking mechanism that is configured to substantially secure the mouthpiece to the reservoir housing when a predetermined length of the hollow pin is received within the airflow tube.

17. A cartridge for a device, the cartridge comprising:

a reservoir housing having a first housing end and a second housing end opposite the first housing end, the reservoir housing being configured to hold vaporizable material;

an airflow tube that extends through the reservoir housing, the airflow tube defining an airflow passageway therethrough;

first and second seals that are each substantially impermeable to fluid, the first seal being substantially secured to the first housing end and the second seal being substantially secured to the second housing end, wherein the first and second seals are configured to be selectively compromised to allow access to the vaporizable material within the reservoir housing for vaporization into vaporized material;

a mouthpiece having an orifice extending therethrough;

a hollow pin extending distally from the mouthpiece and in communication with the orifice; wherein the mouthpiece and the reservoir housing are configured to selectively slide relative to each other to cause the hollow pin to pierce the first seal to thereby place the orifice in communication with the airflow passageway; and a locking mechanism that locks the mouthpiece directly to the reservoir housing of the cartridge in a first position during insertion of at least a portion of the cartridge into the device and until application of a compressive force to at least one of the mouthpiece and the reservoir housing exceeds a predetermined threshold force.

18. The cartridge of claim 17, further comprising another locking mechanism that is configured to secure the mouthpiece to the reservoir housing at a second position when a predetermined length of the hollow pin is received within the airflow tube.

19. The cartridge of claim 17, wherein the second seal is configured to be removed from the second housing end.

20. The cartridge of claim 17, wherein the first and second seals hermetically seal the reservoir housing.

* * * * *